(12) United States Patent
Kavusi et al.

(10) Patent No.: US 9,946,836 B2
(45) Date of Patent: Apr. 17, 2018

(54) BIOMARKER MONITORING DEVICE AND METHOD

(75) Inventors: Sam Kavusi, Menlo Park, CA (US); Christoph Lang, Cupertino, CA (US)

(73) Assignee: Robert Bosch GmbH, Stuttgart (DE)

( * ) Notice: Subject to any disclaimer, the term of this patent is extended or adjusted under 35 U.S.C. 154(b) by 2147 days.

(21) Appl. No.: 13/017,391

(22) Filed: Jan. 31, 2011

(65) Prior Publication Data
US 2012/0197534 A1   Aug. 2, 2012

(51) Int. Cl.
*G01N 33/48* (2006.01)
*G06F 19/28* (2011.01)
*G06F 19/00* (2018.01)

(52) U.S. Cl.
CPC .......... *G06F 19/28* (2013.01); *G06F 19/3431* (2013.01); *G06F 19/3487* (2013.01); *G06F 19/366* (2013.01)

(58) Field of Classification Search
CPC ....................................................... G06F 19/28
USPC ..................................................... 702/19, 20
See application file for complete search history.

(56) References Cited

U.S. PATENT DOCUMENTS

| | | | |
|---|---|---|---|
| 5,660,163 A * | 8/1997 | Schulman et al. | 600/345 |
| 2003/0149593 A1 | 8/2003 | Mok et al. | |
| 2006/0094056 A1 * | 5/2006 | Chappell et al. | 435/7.1 |
| 2008/0033272 A1 * | 2/2008 | Gough et al. | 600/347 |
| 2009/0196852 A1 * | 8/2009 | Watkinson | 424/85.4 |
| 2010/0073202 A1 | 3/2010 | Mazed | |
| 2010/0087630 A1 | 4/2010 | Oelert et al. | |
| 2011/0010257 A1 * | 1/2011 | Hill et al. | 705/26.1 |
| 2011/0034347 A1 * | 2/2011 | Manjili et al. | 506/9 |
| 2011/0230413 A1 * | 9/2011 | Dhib-Jalbut | 514/16.6 |
| 2011/0313680 A1 * | 12/2011 | Doyle et al. | 702/19 |
| 2012/0237954 A1 * | 9/2012 | Duncan | 435/7.24 |

FOREIGN PATENT DOCUMENTS

| | | |
|---|---|---|
| CN | 1586425 A | 3/2005 |
| CN | 201282481 Y | 7/2009 |
| EP | 2017612 A1 | 1/2009 |

(Continued)

OTHER PUBLICATIONS

International Search Report and Written Opinion in corresponding PCT Application (i.e., PCT/US2012/022862), completed Sep. 18, 2012 (10 pages).

(Continued)

*Primary Examiner* — Eman Alkafawi
(74) *Attorney, Agent, or Firm* — Maginot Moore & Beck LLP

(57) ABSTRACT

A biomarker monitoring method and system in one embodiment includes a communications network, a portable wellness device configured to form a communication link with the communications network, the portable wellness device including a detector configured to detect at least one biomarker in a biologic sample, a first memory, a plurality of program instructions stored in the first memory, and a processing circuit operably connected to the first memory and configured to execute the program instructions to generate wellness data based upon detection of the at least one biomarker in the biologic sample, and a remote user interface operably connected to the communications network and configured to render the wellness data.

20 Claims, 6 Drawing Sheets

(56) References Cited

FOREIGN PATENT DOCUMENTS

| JP | H10-505896 A | 6/1998 |
|---|---|---|
| JP | 2003511070 A | 3/2003 |
| TW | 201102045 A | 1/2011 |
| TW | 201128191 A | 8/2011 |
| WO | 02/084249 | 10/2002 |
| WO | 2006026741 A1 | 3/2006 |
| WO | 2006092385 | 9/2006 |
| WO | 2009017697 A2 | 2/2009 |
| WO | 2010072386 A | 7/2010 |
| WO | 2010099607 A1 | 9/2010 |
| WO | 2011109716 A2 | 9/2011 |

OTHER PUBLICATIONS

Izuhara et al., "Microarray-based identification of novel biomarkers in asthma," Allergology International, 2006, pp. 361-367, vol. 55, No. 4, Japan (8 pages).
Bousquet et al., "The public health implications of asthma," Bulletin of the World Health Organization, vol. 83 (2005) 548-554 (7 pages).
Waltraud Eder, Markus J. Ege, and Erica von Mutius, "The asthma epidemic," The New England Journal of Medicine 355, No. 21 (Nov. 23, 2006): 2226-2235 (10 pages).
Claire-Anne Siegrist, "Public health: Autoimmune diseases after adolescent or adult immunization: What should we expect?," CMAJ: Canadian Medical Association Journal 177, No. 11 (Nov. 20, 2007): 1352-1354 (3 pages).
Rudolph Valenta, "The future of antigen-specific immunotherapy of allergy," Nat Rev Immunol 2, No. 6 (Jun. 2002): 446-453 (8 pages).
Mark Larche, Cezmi A. Akdis, and Rudolf Valenta, Immunological mechanisms of allergen-specific immunotherapy, Nat Rev Immunol 6, No. 10 (Oct. 2006): 761-771 (11 pages).
K Gehlhar et al., "Monitoring allergen immunotherapy of pollen-allergic patients: the ratio of allergen-specific IgG4 to IgG1 correlates with clinical outcome," Clinical and Experimental Allergy: Journal of the British Society for Allergy and Clinical Immunology 29, No. 4 (Apr. 1999): 497-506 (10 pages).
Leroy Hood et al., "Systems Biology and New Technologies Enable Predictive and Preventative Medicine," Science 306, No. 5696 (Oct. 22, 2004): 640-643 (4 pages).
Robert F. Service, "Proteomics: Proteomics Ponders Prime Time," Science, vol. 321, No. 5897 (Sep. 26, 2008): 1758-1761 (4 pages).
Stephen F Kingsmore, "Multiplexed protein measurement: technologies and applications of protein and antibody arrays," Nature Reviews. Drug Discovery 5, No. 4 (Apr. 2006): 310-320 (23 pages).
Michael F. Holick, "Vitamin D: importance in the prevention of cancers, type 1 diabetes, heart disease, and osteoporosis," The American Journal of Clinical Nutrition 79, No. 3 (Mar. 2004): 362-371 (10 pages).
Maria-Grazia Roncarolo and Manuela Battaglia, "Regulatory T-cell immunotherapy for tolerance to self antigens and alloantigens in humans," Nat Rev Immunol 7, No. 8 (2007): 585-598 (14 pages).
Stephen R. Durham and Stephen J. Till, "Immunologic changes associated with allergen immunotherapy," Journal of Allergy and Clinical Immunology 102, No. 2 (Aug. 1998): 157-1 (8 pages).
Parris KilDD, "Th1/Th2 balance: the hypothesis, its limitations, and implications for health and disease," Alternative Medicine Review: vol. 8, No. 3 (Aug. 2003): 223-246 (24 pages).
Stephen C. Jameson, "Maintaining the norm: T-cell homeostasis," Nat Rev Immunol vol. 2, No. 8 (2002): 547-556 (10 pages).
Erin Fitch et al., "Pathophysiology of psoriasis: Recent advances on IL-23 and Th17cytokines," Current Rheumatology Reports 9, No. 6 (Dec. 1, 2007): 461-467 (7 pages).
Heiko Hawlisch et al., "The anaphylatoxins bridge innate and adaptive immune responses in allergic asthma," Molecular Immunology 41, No. 2-3 (Jun. 2004): 123-131 (9 pages).
Ying Lin et al., "Profiling of human cytokines in healthy individuals with vitamin E supplementation by antibody array," Cancer Letters 187, No. 1-2 (Dec. 10, 2002): 17-24 (8 pages).
S C Castle, "Clinical relevance of age-related immune dysfunction," Clinical Infectious Diseases: An Official Publication of the Infectious Diseases Society of America 31, No. 2 (Aug. 2000): 578-585 (8 pages).
A B Kay, "Allergy and allergic diseases. First of two parts," The New England Journal of Medicine 344, No. 1 (Jan. 4, 2001): 30-37 (8 pages).
D M Pardoll, "Paracrine cytokine adjuvants in cancer immunotherapy," Annual Review of Immunology 13 (1995): 399-415 (17 pages).
Mubeccel Akdis et al., "Immune Responses in Healthy and Allergic Individuals Are Characterized by a Fine Balance between Allergen-specific T Regulatory 1 and T Helper 2 Cells," J. Exp. Med. 199, No. 11 (Jun. 7, 2004): 1567-1575 (9 pages).
Emma Guttman-Yassky et al., "Low expression of the IL-23/Th17 pathway in atopic dermatitis compared to psoriasis," Journal of Immunology (Baltimore, Md.: 1950) 181, No. 10 (Nov. 15, 2008): 7420-7427 (8 pages).
H Nakashima et al., "Serum chemokine profile in patients with bullous pemphigoid," The British Journal of Dermatology 156, No. 3 (Mar. 2007): 454-459 (16 pages).
Zhifang Zhang et al., "High plasma levels of MCP-1 and eotaxin provide evidence for an immunological basis of fibromyalgia," Experimental Biology and Medicine (Maywood, N.J.) 233, No. 9 (Sep. 2008): 1171-1180 (10 pages).
Cottingham, Katie, "Basic and clinical researchers: the great divide?" Journal of Proteome Research, vol. 7, No. 3 (Mar. 7, 2008), pp. 840-843 (4 pages).
Humphery-Smith et al., "The search for validated biomarkers in the face of biosystems complexity," Drug Discovery World Spring 2005, pp. 49-56 (8 pages).
Lin et al., "Irrational Exuberance in Clinical Proteomics," Clinical Cancer Resarch 2005; 11 (Nov. 15, 2005), pp. 7963-7964 (2 pages).
M Wills-Karp, J. Santeliz, and C L Karp, "The germless theory of allergic disease: revisiting the hygiene hypothesis," Nature Reviews. Immunology 1, No. 1 (Oct. 2001): 69-75 (7 pages).
English Translation of Chinese Search Report and Written Opinion corresponding to Chinese Application 20128001111.30, dated Mar. 2, 2016 (15 pages).
Li, Fang-Xu et al., "Formaldehyde-mediated Chronic Damage May Be Related to Sporadic Neurodegeneration", Progress in Biochemistry and Biophysics, vol. 35, No. 4, pp. 393-400 (8 pages), Apr. 8, 2008.
English translation of Japanese Search Report and Written Opinion corresponding to Japanese Application No. 2013-552562, dated Sep. 9, 2015 (5 pages).
English translation of Chinese Search Report and Written Opinion corresponding to Chinese Application No. 201280011113.0, dated Jun. 26, 2015 (13 pages).
English translation of Taiwanese Search Report and Written Opinion corresponding to Taiwanese Application No. 101103000, dated Oct. 13, 2015 (3 pages).

* cited by examiner

# BIOMARKER MONITORING DEVICE AND METHOD

FIELD

This invention relates to wearable monitoring devices.

BACKGROUND

Allergies and asthma have become highly prevalent in the western world. Allergies and asthma now affect about one out of every four Americans, which is three times the number of people suffering from diabetes. Moreover, the prevalence of allergies and asthma has seen a significant increase since about 1960 as reported, for example, by Waltraud Eder, et al., "The asthma epidemic," *The New England Journal of Medicine* 355, no. 21 (Nov. 23, 2006), pages 2226-2235. Allergies and asthma are two examples of ailments which result from weakened or stressed immune systems.

Health problems associated with weakened or stressed immune systems are frequently exacerbated by the failure of individuals to understand the status of their immune system or factors influencing the status of their immune system. This lack of understanding is discussed, for example, by M Wills-Karp, et al. "The germless theory of allergic disease; revisiting the hygiene hypothesis," *Nature Reviews. Immunology* 1, no. 1 (October 2001), pages 69-75, and Claire-Anne Siegrist, "Public health: Autoimmune diseases after adolescent or adult immunization: What should we expect?," *CMAJ: Canadian Medical Association Journal* 177, no. 11 (Nov. 20, 2007), pages 1352-1354.

Treatment of chronic diseases and ailments is also adversely affected by lack of insight into the status of an individual's immune system. For example, when pursuing allergen specific immunotherapy the lack of insight into the individual's immune system increases risks associated with the treatment or necessitates increased medical supervision and subsequent costs. Such adverse effects are discussed, for example, by Rudolf Valenta, "The future of antigen-specific immunotherapy of allergy," *National Review of Immunology* 2, no. 6 (June 2002), pages 446-453, and Mark Larche, et al., "Immunological mechanisms of allergen specific immunotherapy," *National Review of Immunology* 6, no. 10 (October 2006), pages 761-771.

In a clinical setting, the reaction of the immune system of an individual's environment or exposure to a substance can be inferred by analysis of various biomarkers such as chemokines and cytokines as reported by K Gelhar, et al., "Monitoring allergen immunotherapy of pollen-allergic patients: the ratio of allergen specific IgG4 to IgG1 correlates with clinical outcome," *Clinical and Experimental Allergy: Journal of the British Society for Allergy and Clinical Immunology* 29, no. 4 (April 1999), pages 497-506.

While detection of the levels of chemokines and cytokines in a biological sample has traditionally required large pieces of equipment, recent advances have enabled diagnostic tests that can be performed at the point of care of an individual, such as at the bedside of a patient, at a care provider location, or at the home of the patient. The promise of such diagnostic tests is described, for example, by Leroy Hood et al., "Systems Biology and New Technologies Enable Predictive and Preventative Medicine," *Science* 306, no. 5696 (Oct. 22, 2004): 640-643. Depending upon the particular diagnostic test, the substance tested may be human body fluids such as blood, serum, saliva, biological cells, urine, or other biomolecules. Diagnostic tests are not, however, limited to biomolecules since testing may be further desired on consumables such as milk, baby food, or water.

Many diagnostic testing devices incorporate affinity based sensors which are considered to be the state-of-the-art in detection of biomarkers. Affinity based sensors function according to a "key-lock" principal in which a molecule with very high association factor to the marker of interest is used for detection. For example, a pregnancy test kit may incorporate a monoclonal antibody specific to a β-subunit of hCG (βhCG). The antibody is conjugated with a tag, e.g., gold, latex, or fluorophore, which is used for detection. If the targeted molecule binds with the conjugated antibody, the tagged key-lock pair will be detectable such as by a visible test line.

ELISA plates and microarrays (e.g., Nucleic Acid, peptide, and protein) incorporate a similar principal. FIG. 1 depicts an ELISA assay 10 wherein antibodies 12 are immobilized on a substrate 14. The substrate 14 may be positioned within a well (not shown). A blocker 16 is provided to cover the surface of the substrate around the antibody 12. In a typical ELISA assay, a sample 18 is then added to the well in which the primary antibody 12 is immobilized. Next, the sample is incubated for some time. During incubation, the blocker 16 prevents the molecules of interest in the sample from binding to the surface of the substrate 14 in order to avoid false binding. During incubation, some of the molecules of interest 18 become bound with some of the antibodies 12 as depicted in FIG. 2. After incubation, the remaining sample is washed to remove the unbound primary antibodies 18.

Subsequently, a secondary antibody 20 with a bound label 22 is added to the well, incubated, and washed resulting in the configuration of FIG. 3. As depicted in FIG. 3, the labeled secondary antibodies 20 are bound to the molecules of interest 18 that are in turn bound to the antibodies 12. Accordingly, the number of labels 22 bound by the antibodies 20 to the antigen 18 is proportional to the concentration of the target antigen. Depending on the label used, the number of labels can be finally detected using colorimetry, amperometry, magnetometry, voltammetry, luminescence, or fluorescence detection. Other label-free antibody processes such as surface plasmon resonance may alternatively be used.

Accordingly, there is a need for a system and method that allow self monitoring of an individual's immune system. A further need exists for a system including a portable device which can be used to provide insight into the immune system of an individual. It would be further beneficial if such a device could be worn by the individual.

SUMMARY

A physical activity monitoring method and system in one embodiment includes a communications network, a portable wellness device configured to form a communication link with the communications network, the portable wellness device including a detector configured to detect at least one biomarker in a biologic sample, a first memory, a plurality of program instructions stored in the first memory, and a processing circuit operably connected to the first memory and configured to execute the program instructions to generate wellness data based upon detection of the at least one biomarker in the biologic sample, and a remote user interface operably connected to the communications network and configured to render the wellness data.

In accordance with another embodiment, a biomarker monitoring system includes a communications network, a wearable detector device operably connectable to the communications network and configured to detect at least one biomarker in a biologic sample, a memory operably connected to the communications network, a plurality of program instructions stored in the memory, a processing circuit operably connected to the communications network and configured to execute the program instructions to generate wellness data indicative of the status of an immune system based upon detection of the at least one biomarker in the biologic sample, and a user interface operably connected to the processing circuit for rendering the wellness data.

DESCRIPTION

Figure 1:
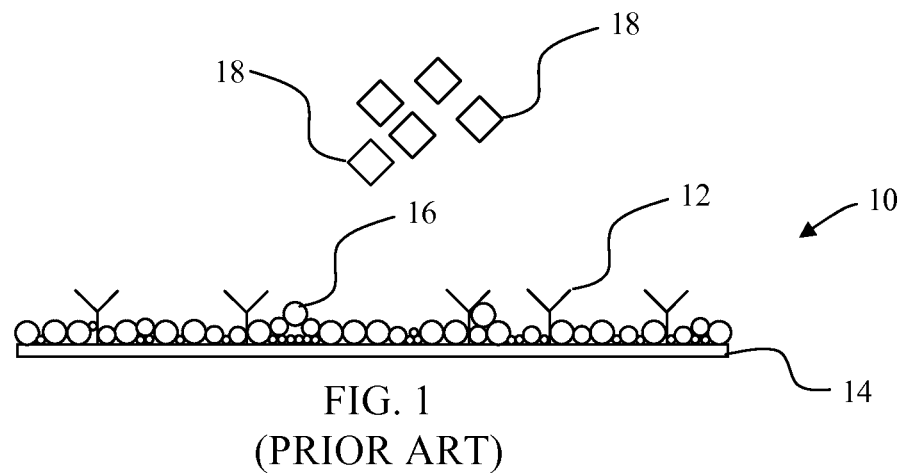
FIG. 1 depicts a schematic of a prior art test site within an ELISA array with an antibody and blockers formed on a substrate as a sample is added to the test site.
Figure 2:
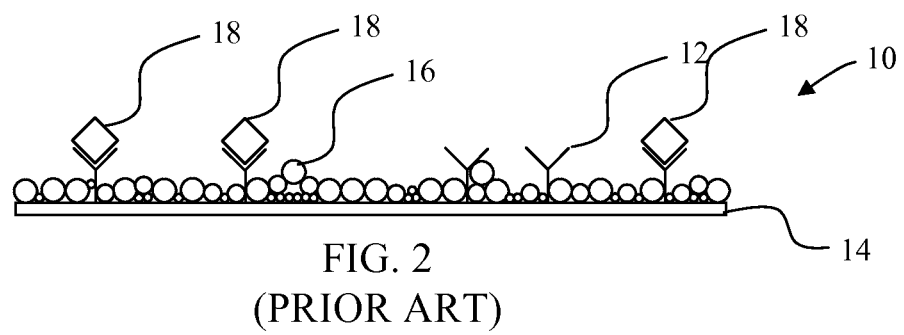
FIG. 2 depicts the test site of FIG. 1 with a molecule of interest bound to some of the antibodies of FIG. 1 after the test site has been incubated and washed.
Figure 3:
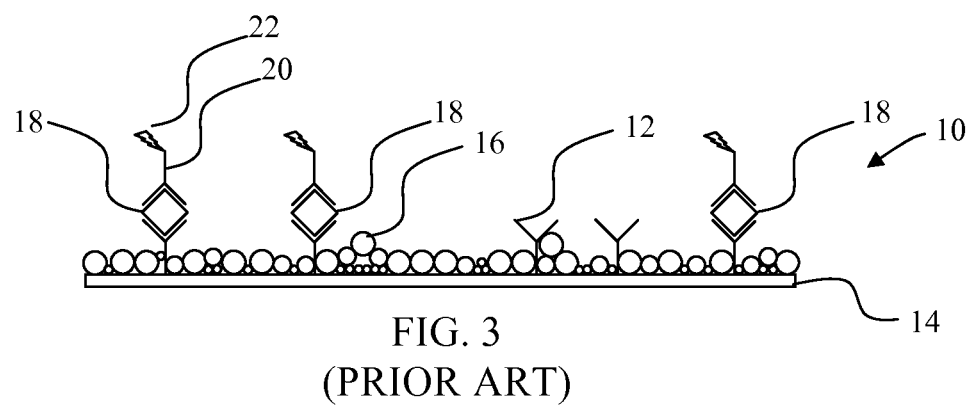
FIG. 3 depicts the test site of FIG. 2 after a labeled secondary antibody has been added and the test site has again been incubated and washed so that the labeled secondary is bound to the bound molecules of interest.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 4:
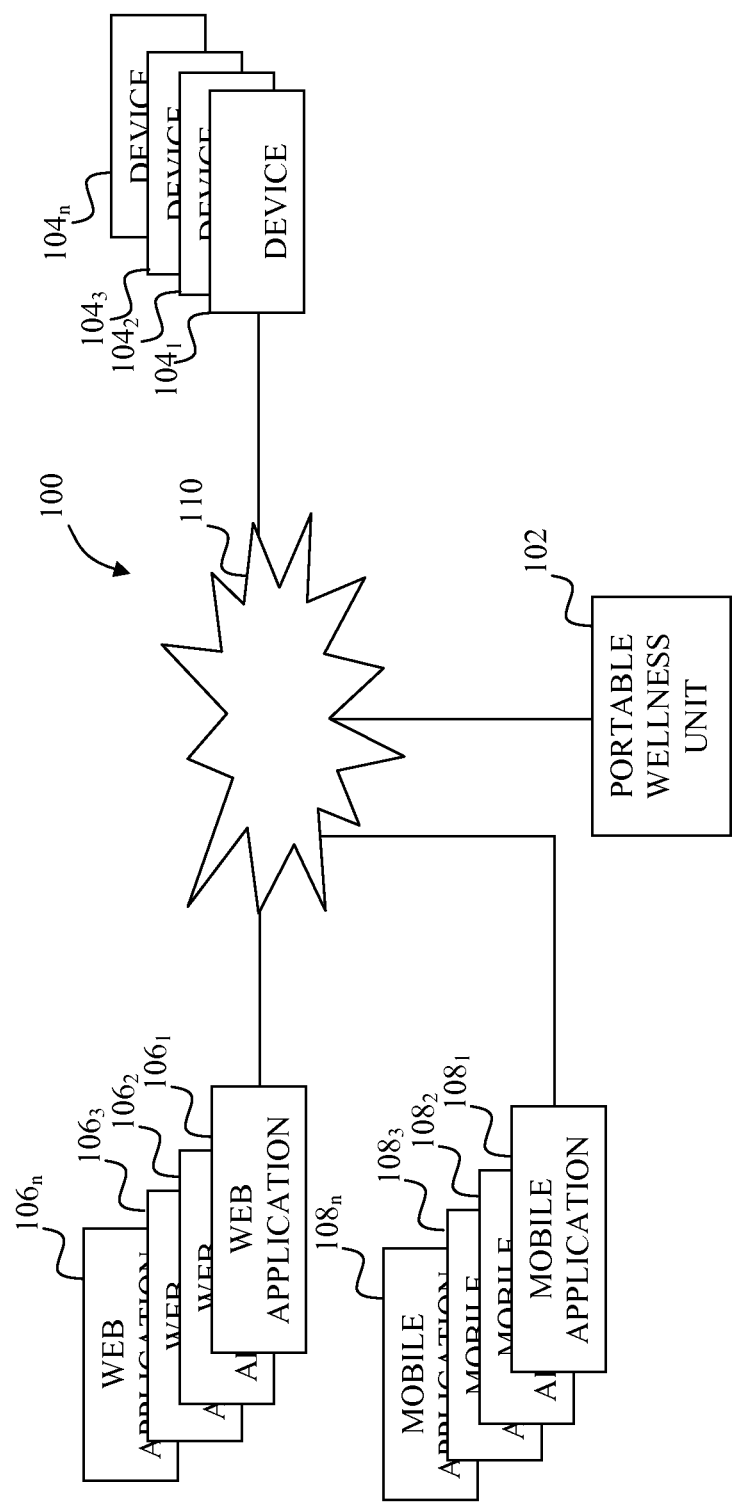
FIG. 4 depicts a block diagram of a biomarker monitoring network including a portable wellness unit that may be wearable in accordance with principles of the present invention.

Referring to FIG. 4, there is depicted a representation of a biomarker monitoring network generally designated 100. The network 100 includes a portable wellness unit 102, other devices $104_x$, web applications 106 and mobile applications 108. The portable wellness unit 102, other devices $104_x$, web applications 106 and mobile applications 108 are operably connected to a communications network 110.

The communications network 110 in one embodiment is a seamless wireless network such as the internet or a cellular telephone network. In such embodiments, the components in the biomarker monitoring network 100 may be configured to utilize available Wi-Fi networks to connect to the internet. The components in the biomarker monitoring network 100 may further or alternatively be configured to access the communications network 110 directly through a wireless system like a cellular telephone network or in conjunction with the internet.

The other devices $104_x$ may include portable wellness units, a user interface, graphical user interface, keyboards, pointing devices, remote and/or local communication links, displays, and other devices that allow externally generated information to be provided to the biomarker monitoring network 100, and that allow internal information of the biomarker monitoring network 100 to be communicated externally.

Figure 5:
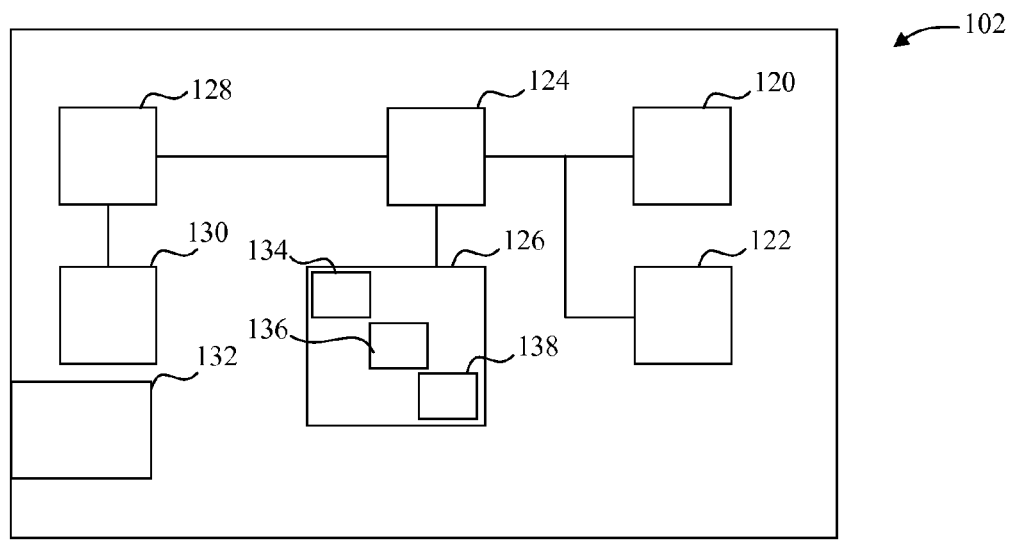
FIG. 5 depicts a schematic of a wearable wellness unit of FIG. 4 including at least one communication circuit and detector electronics.

The wellness unit 102 is described in more detail with reference to FIG. 5. The wellness unit 102 includes a network interface 120, an I/O portion 122, a processor 124, a non-volatile memory 126, a signal processing circuit 128, and detector electronics 130. A test port 132 is operably connected to or positioned with respect to the detector electronics 130. The network interface 120 is a communication circuit that effectuates communication with the communications network 110. The network interface 120 is further operable to, either alone or in conjunction with the processor 124, interpret messages in wireless communications received from the communications network 110. In some embodiments, the network interface 120 may include a wired interface for use either alone or in conjunction with wireless capabilities to connect to the communications network 110.

The I/O portion 122 may include a graphical user interface, a keyboard, a pointing device, remote and/or local communication links, displays, and other devices that allow externally generated information to be provided to the portable wellness unit 102, and that allow internal data of the portable wellness unit 102 to be communicated externally.

The processor 124 may suitably be a general purpose computer processing circuit such as a microprocessor and its associated circuitry. The processor 124 is operable to control the general operation of the portable wellness unit 102 and to carry out the operations attributed to it herein.

The programmable non-volatile memory 126, which may be embodied as a flash programmable EEPROM, stores configuration information for the detector electronics 130. The programmable non-volatile memory 126 includes an "address" or "ID" of the portable wellness unit 102 that is appended to any communications generated by the portable wellness unit 102. The memory 126 further includes set-up configuration information related to the system communication parameters employed by the processor 124 to transmit information to the communications network 110. Within the memory 126 is a detector control program 134 and program instructions 136. The detector control program 134 and program instructions 136, which are described more fully below, are executable by the processor 124 and/or any other components as appropriate. A factors database 138 is also located within the memory 126.

The signal processing circuit 128 includes circuitry that interfaces with the detector electronics 130, converts analog detector signals to digital signals, and provides the digital signals to the processor 124. In general, the processor 124 receives digital detector information from the signal processing circuit 128 and provides the information to the communication network 110.

The detector electronics 130 in this embodiment includes a label reader. The label reader is configured to detect a signal associated with the concentration of a molecule of interest in a sample that is provided to one or more test sites of a sample collector which is either inserted into or provided by the test port 132. The type of sensor or sensors incorporated into the detector electronics 130 will vary depending upon the particular label used for a particular molecule of interest as discussed more fully below. Various embodiments may thus use luminescence, fluorescence, colorimetric, electrochemical, impedance, and magnetic sensors. The sample collector may be provided in the form of a variety of test site platforms including 96-well plates, plates with fewer or additional wells, microarray platforms, printed circuit board platforms, CMOS chip platforms, multiplexed assays, protein arrays, lateral flow devices, sandwich assays, competitive assays, bead based arrays or other appropriate platforms.

While the biomarker monitoring network 100 depicts one arrangement of a biomarker monitoring network, the various components described above may be configured in a number of alternative networks. By way of example, the factors database 138 and some program instructions 136 may be stored within the web applications 106 or mobile applications 108. In such an embodiment, the portable wellness unit 102 may be configured to access the web applications 106 or mobile applications 108 using one or more of the internet, a wireless cellular network, a local area network, or a wide area network. In such an embodiment, some of the functionality described in association with the portable wellness unit 102 may be provided in the web applications 106 or mobile applications 108. The portable wellness unit 102 in such an embodiment may be configured to obtain a limited number of samples and to communicate the sample data a limited number of times. For example, the portable wellness unit 102 may be provided with sufficient power to make only a single communication.

Figure 6:
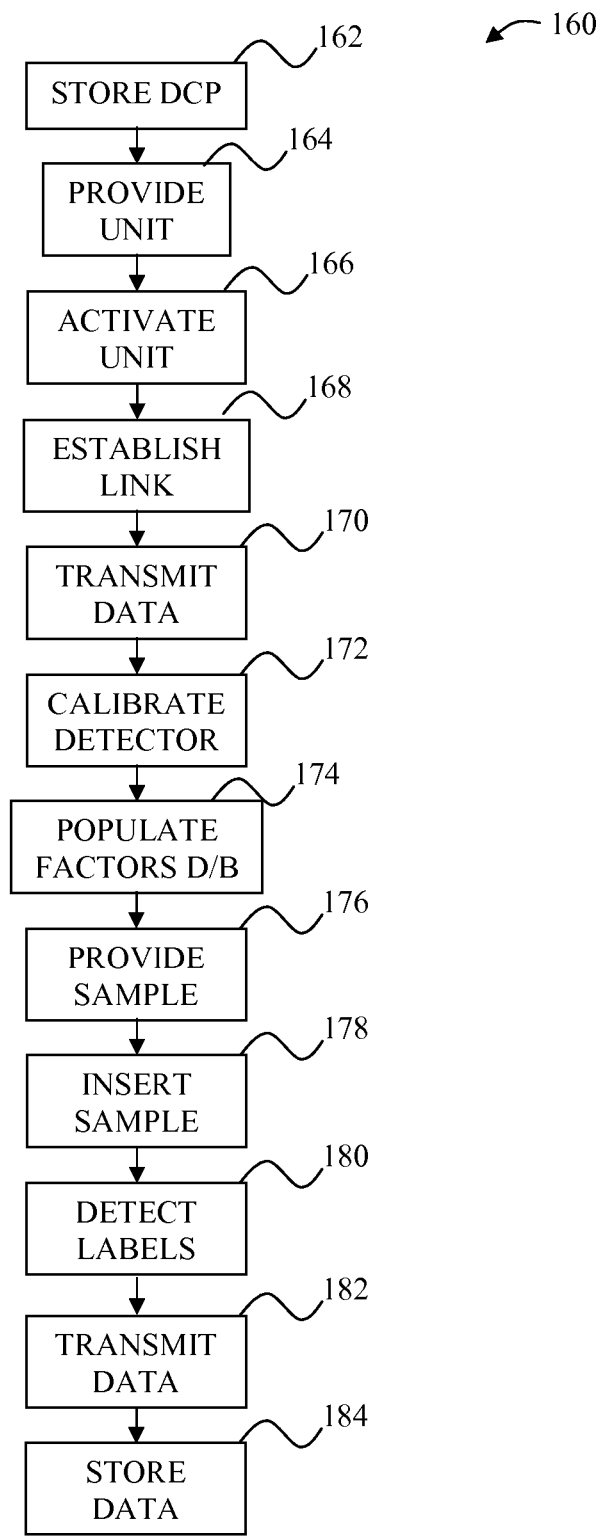
FIG. 6 depicts a process that may be controlled by the processor of FIG. 4 for obtaining biomarker data from the portable wellness units of FIG. 5 for use in generating wellness data indicative of the status of an individual's immune system.

Referring to FIG. 6, there is depicted a flowchart, generally designated 160, setting forth an exemplary manner of operation of the network 100. Initially, the detector control program (DCP) 134 may be stored within the memory 1126 (block 162). The detector control program 134 includes detector control program instructions for electronic control of the detector electronics 130. The detector control program instructions allow the processor 124 to control operation of the detector electronics 130 including performance of calibration procedures. Additionally or alternatively, the detector control program instructions may be provided in other components of the biomarker monitoring network.

Next, a portable wellness unit 102 is provided to a user (block 164). The portable wellness unit 102 is then activated (block 166). Upon activation of the portable wellness unit 102, the processing circuit 106 initiates' data capture subroutines. Additionally, the processing circuit 102 establishes a link with the communications network 110 (block 168). Alternatively, the portable wellness unit 102 may establish a link with the communications network 110 at a later point in the process.

Initial output from the detector electronics 120 is passed through the signal processing circuit 128 to the processor 124 (block 170). The initial sensor data is used by the processor 124 to calibrate the detector electronics 120 (block 172).

The factors database 138 is then populated (block 174). The data used to populate the factors database 138 may be input from one or more of the other devices $104_x$. Alternatively, the I/O portion 122 may be used by the wearer of the portable wellness unit 102 to input factors data.

The wearer then provides a biologic sample (block 176). The form of the biologic sample depends upon the particular biomarkers to be detected. The biologic sample may be in the form of human body fluids such as blood, serum, saliva, biological cells, urine, or other biomolecules. The biologic sample is provided on a suitable sample platform which is inserted into the test port 132 (block 178).

The detector control program instructions, when executed by the processor 124, control the detector electronics 130 to process the biologic sample and detect labels attached to capture molecules having an affinity to a biomarker of interest (block 180). In one embodiment, the detector electronics 130 are controlled to detect labels indicative of the concentration of Th1, Th2, and regulatory Tr1 cells. The concentration of these cells can be inferred based upon their cytokine profile as Th1 cells secrete IFNγ, Th2 cells secrete IL-4, IL-5, and IL-13, and Tr1 cells secrete IL-10 and TGFβ. Depending upon the particular individual, the biomarker may be one or more of various cytokines, chemokines, metalloproteinase, toxicity biomarkers or antigens. Some specific examples are IFNγ, IL-2, IL-4, IL-5, IL-7, IL-9, IL-10, IL-12, IL-15, IL-21, IL-22, IL-23, TGFβ, TNFβ, MCP-1, IgG1-4, IgE, and IgM.

The biomarker detector data is passed through the signal processing circuit 128 to the processor 124 (block 182). The biomarker detector data is processed by the processor 124 and stored along with a date/time stamp in the memory 126 (block 184). By way of example, data associated with inferred concentrations of Th1, Th2, and Tr1 cells may be stored in the memory 126 along with a date/time stamp indicating when the biologic sample was processed.

The foregoing actions may be performed in different orders. By way of example, factors may be stored prior to providing a wellness unit 102 to a subject. Additionally, the various actions may be performed by different components of the network 100. By way of example, in one embodiment, the output of the detector electronics 130 may be transmitted to a remote location such as a server remote from the sensor for storage.

The portable wellness unit 102 is configured to provide wellness data which as used herein means data related to the immune system status of an individual based upon biomarker detector data. The wellness data is provided for example, by transmitting data over the communications network 110 for display by a device $104_x$. The wellness data may be provided as feedback either in real time or at another time selected by the wearer or other authorized individual by access through a device $104_x$. The wellness data based upon the biomarker detector data may be combined with other data as discussed more fully below. In one embodiment, the wellness data is provided through the I/O portion 122 of the portable wellness unit 102.

Figure 7:
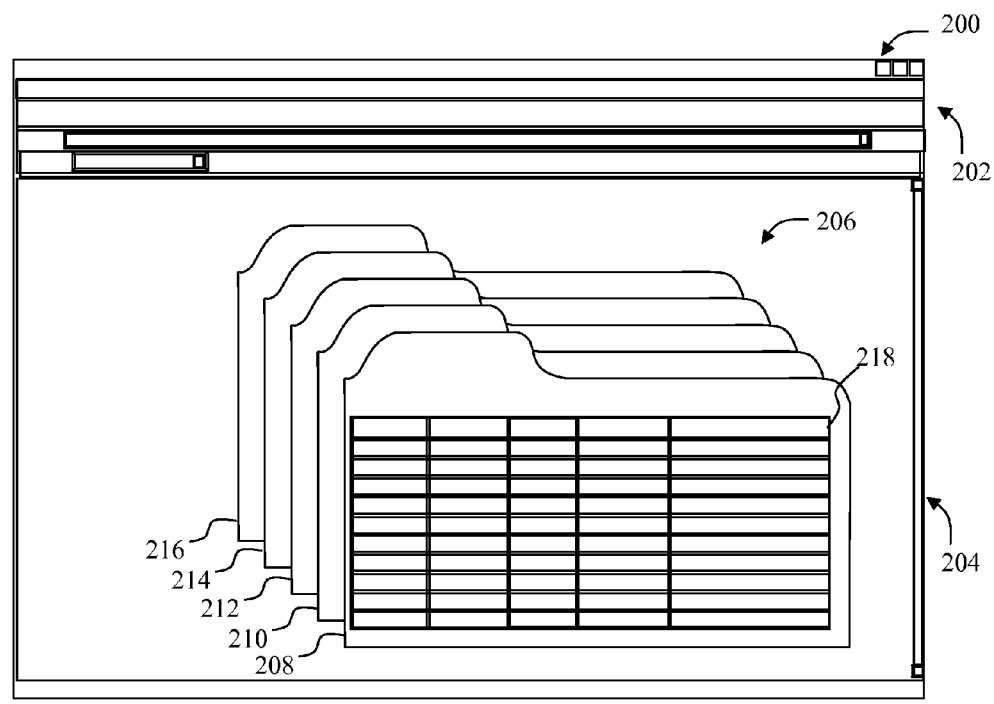
FIG. 7 depicts a screen that may be generated by a portable wellness unit or transmitted over a communications link such as the Internet and used to display biomarker data from the portable wellness unit of FIG. 4 along with wellness data generated by the processor of FIG. 4.

A screen which may be used to provide wellness data based upon detector data stored in the memory 126, such as when the data is accessed by a device $104_x$ connected to the memory 126 by an internet connection, is depicted in FIG. 7. The screen 200 includes a navigation portion 202 and a data portion 204. A number of folders 206 are rendered within the data portion 204. The folders 206 in one embodiment are associated with different individuals. In another embodiment, the folders are each associated with a single individual. For purpose of this example, each of the folders 206 is associated with a single individual and may be rendered by the I/O portion 122 of the portable wellness unit 102.

The folders 206 include a summary folder 208, a first allergen folder 210, a second allergen folder 212, an asthma folder 214, and a cancer folder 216. The summary folder 208 includes a chart 218. Data that may be rendered on the chart 248 include identification of the individual or subject associated with the portable wellness unit 102, summary wellness data, and other desired data.

Figure 8:
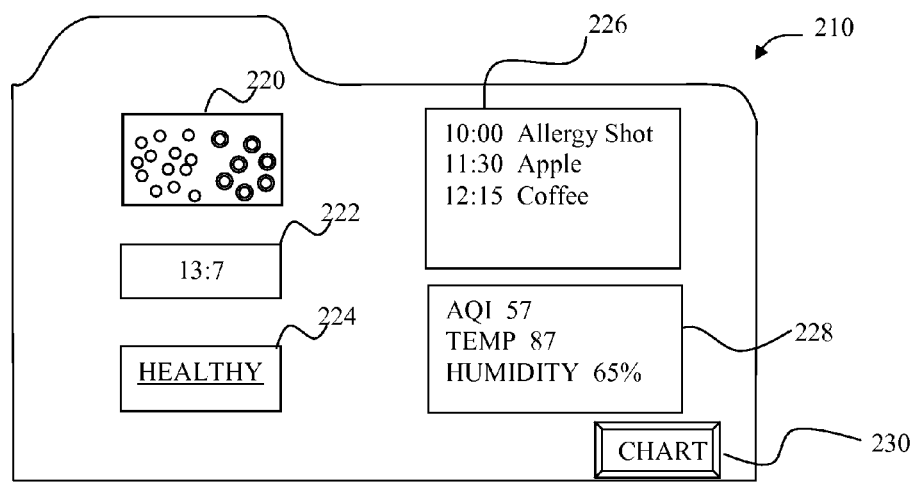
FIG. 8 depicts the contents of an exemplary wellness data folder rendered within the screen of FIG. 7.

By selecting the first allergen folder 210, the first allergen folder 210 is moved to the forefront of the screen 200. When in the forefront, a viewer observes the first allergen folder 210 as depicted in FIG. 8. The first allergen folder 210 displays wellness data related to the immune system of the subject based upon reactions to a first allergen. In this embodiment, the first allergen folder 210 displays data fields 220, 222, and 224 which are used to display a visual representation of the subject's Th1/Th2 ratio, a numerical metric of the subject's Th1/Th2 ratio, and a word descriptor of the wellness of the subject's immune system, respectively. The data fields presented may be modified. For example, one or more data fields may be used to indicate other biological parameters of the individual such as respiration rate, heart beat rate, and blood oxygen content. If desired, the detector electronics 130 may include sensors to detect the biological parameters.

The first allergen folder 210 further identifies personal factors in a personal factors window 226 and environmental factors in an environmental factors window 228. Personal factors are factors unique to the individual which may affect the subject's immune system. Personal factors may include the administration of a drug, type of activity the individual is engaged in such as hiking, sleeping, etc., and food intake. Some personal factors such as temperature, heart rate, and respiration rate, may be obtained from sensors provided within the detector electronics 130. Other personal factors may be provided by devices $104_k$ or by I/O portion 122. For example, the portable wellness unit 102 may be configured to operably connect to a device such as a continuous positive airway pressure (CPAP) device to obtain sleep data.

Environmental factors are factors that are not unique to the individual but which may affect the subject's immune system. Environmental factors include pollutants in the air such as the first allergen, air temperature, humidity, etc. If desired, the environmental factors may include the individual's physical location. In some embodiments, the detector electronics 130 include sensors to obtain the data from which the environmental factors are determined. The detector electronics 130 may thus include temperature sensors, humidity sensors, etc. A GPS sensor in the portable wellness unit 102 or data obtained from a relay station may be used to provide physical location data.

Figure 9:
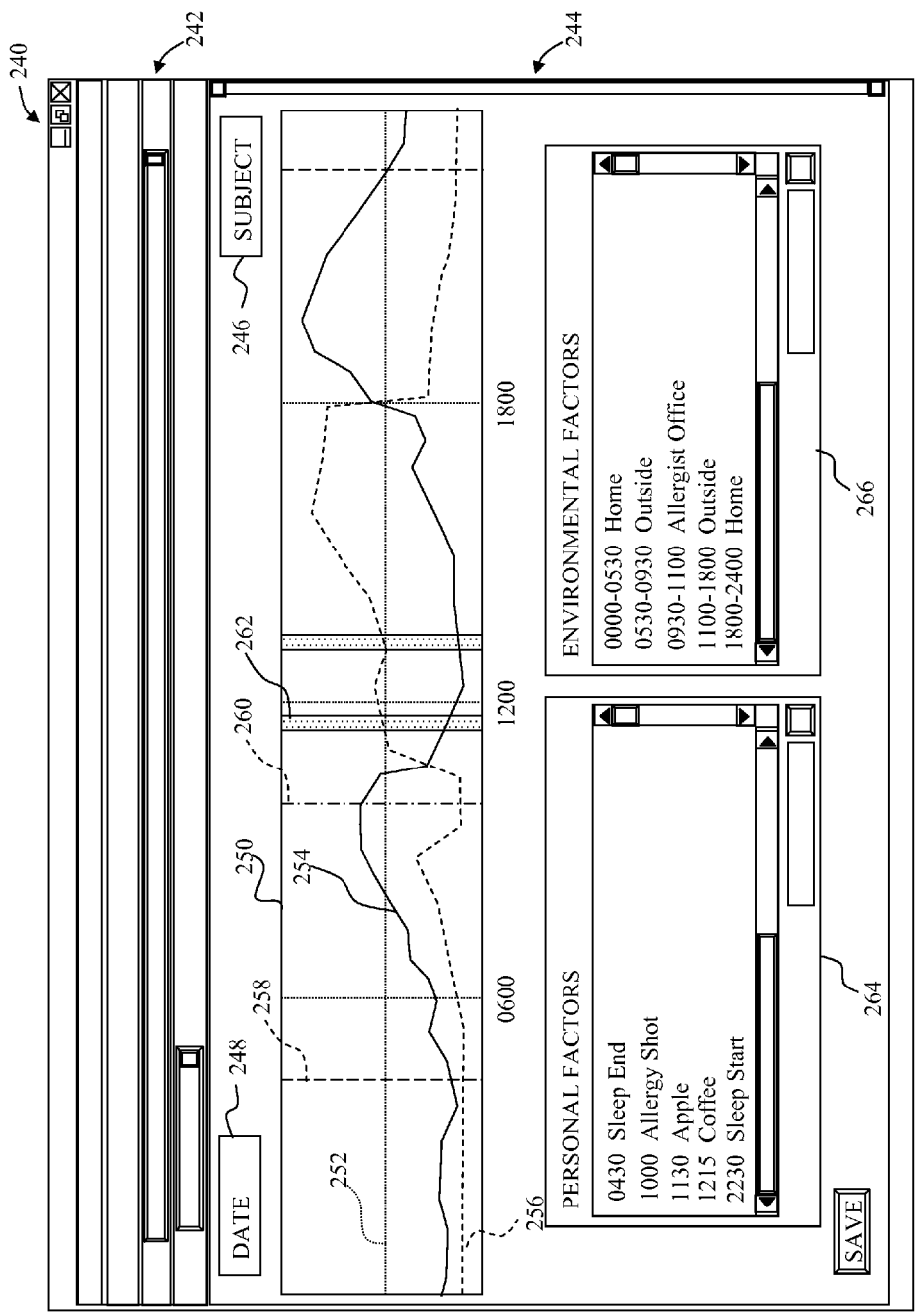
FIG. 9 depicts a screen that may be accessed by a user to review immune system wellness of a subject over a twenty-four hour period including a graphic display of immune system status and personal and environmental factors.

A variety of different screens may be used to display data obtained from the memory 126. Additionally, the data selected for a particular screen, along with the manner in which the data is displayed, may be customized for different applications. By way of example, in this embodiment, the first allergen folder 210 further includes a daily chart button 230. Selection of the daily chart button 230 causes a screen 240 to be rendered as shown in FIG. 9. The screen 240 may be used to provide an easily navigable interface for reviewing activities over a twenty-four hour window.

The screen 240 includes a navigation portion 242 and a data portion 244. The data portion 244 includes an identification field 246 for identifying the subject and a data field 248 which displays the date associated with the data in the data portion 244.

A daily immune system condition chart 250 within the data portion 244 includes a line 252 illustrating a threshold of Th1:Th2 below which the immune system is considered to be healthy. The actual immune system wellness of the individual over a twenty-four hour period is identified by the wellness line 254. The chart 250 further includes representations of personal factors and environmental factors which may influence the health of the individual's immune system.

Depending upon the nature of the factor, the factor may be represented in the chart 250 by a horizontal line, a vertical line, or a band. By way of example, the generally horizontal line 256 may be used to represent the air quality to which the individual is exposed while the vertical lines 258 and 260 respectively indicate the times at which the individual awoke and received an allergy shot. The band 262 is used to identify a time frame over which an apple was eaten by the individual. If desired, more or fewer personal and environmental factors may be rendered on the chart 250 to allow an individual to better ascertain the salient factors influencing immune system wellness.

The data rendered in the chart 250 may be obtained from data stored in the memory 126 such as in the factors database 138. The stored data may be obtained from data generated by the detector electronics 130 as well as from data input through one or more of the devices $104_x$ or the I/O portion 122. By way of example, the screen 240 further includes editable data fields 264 and 268. The editable data fields 264 and 268 allow a user to add or modify information related to personal factors and environmental factors, respectively. For example, by selecting the editable data field 264, a user may enter a date, time, and amount of a medication that was or will be taken.

Various functionalities may be incorporated into the screen 240 in addition to the functions set forth above so as to provide increased insight into the habits of a subject and the effect of those habits on the individual's immune system. Moreover, the biomarker monitoring network 100 may be used in a variety of scenarios. In addition to monitoring biomarkers to provide insight of an individual's immune system during normal activities, the biomarker monitoring network 100 may be used in conducting trials both formal and informal. The ability to access applications such as the web applications 106 and the mobile applications 108 through, and share data with, the devices $104_x$ enables a variety of different hypothesis to be tested either by an individual wearing the portable wellness unit 102 or by a researcher accessing data through a device $104_x$. The portable wellness unit 102 may further be used by a treating physician to track the reaction of an individual to a prescribed medication.

The data obtained from a portable wellness unit 102 can also be aggregated with the data from other portable wellness units 102 associated with other individuals to provide a number of different functionalities. For example, once patient specific data has been removed, the aggregate data may be made accessible to members of the general public. Thus, prior to travelling to a location, an individual known to react to a particular allergen, such as pollen, may access a database storing the aggregate data to determine if that allergen is of concern at the location based upon the biomarkers of individuals currently at that location.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A biomarker monitoring system comprising:
   a communications network;
   a portable wellness device configured to form a communication link with the communications network, the portable wellness device including
      a detector configured to detect at least one biomarker in a biologic sample,
      a first memory,
      a plurality of program instructions stored in the first memory, and
      a processing circuit operably connected to the first memory and configured to execute the program instructions to generate wellness data over a period of time based upon detection of the at least one biomarker in the biologic sample; and
   a remote user interface operably connected to the communications network and configured to render the wellness data, wherein the rendered wellness data depicts a variation associated with the at least one biomarker during the period of time along with one or more of a depiction of a variation of a personal factor which may influence the health of an immune system during the period of time and depiction of a variation of an environmental factor which may influence the health of the immune system during the period of time.

2. The system of claim 1, wherein the portable wellness device includes a portable user interface and the processing circuit is further configured to execute the program instructions to render the wellness data with the portable user interface.

3. The system of claim 2, wherein the wellness data comprises quantitative data.

4. The system of claim 1, further comprising a second memory remote from the first memory, the second memory operably connected to the communications network, wherein the remote user interface renders wellness data stored in the second memory.

5. The system of claim 1, wherein the at least one biomarker comprises:
   at least one first biomarker associated with a T helper 1 (Th1) cell;
   at least one second biomarker associated with a T helper 2 (Th2) cell; and
   at least one third biomarker associated with a T regulatory cell.

6. The system of claim 5, wherein each of the at least one first biomarker and the at least one second biomarker comprises a cytokine, a chemokine, a metalloproteinase, a toxicity biomarker, or an antigen.

7. The system of claim 5, wherein the wellness data is associated with the relative amount of the T helper 1 (Th1) cell and the T helper 2 (Th2) cell in the biologic sample.

8. The system of claim 7, wherein the depicted variation associated with the at least one biomarker comprises a depiction of the relative amount of the T helper 1 (Th1) cell and the T helper 2 (Th2) cell during the period of time.

9. The system of claim 8, wherein the wellness data comprises both the depiction of the variation of the personal factor during the period of time and the depiction of the variation of the environmental factor during the period of time one.

10. The system of claim 9, wherein the personal factor comprises one or more of:
    a sleep period;
    a medication; or
    a consumption.

11. The system of claim 9, wherein the environmental factor comprises one or more of:
    a location;
    an environmental condition; or
    an activity.

12. A biomarker monitoring system comprising:
    a communications network;
    a wearable detector device operably connectable to the communications network and configured to detect at least one biomarker in a biologic sample;
    a memory operably connected to the communications network;
    a plurality of program instructions stored in the memory;
    a processing circuit operably connected to the communications network and configured to execute the program instructions to generate wellness data indicative of the status of an immune system over a period of time based upon detection of the at least one biomarker in the biologic sample; and
    a user interface operably connected to the processing circuit and configured to render the wellness data in the form of a variation associated with the at least one biomarker during the period of time along with one or more of a depiction of a variation of a personal factor during the period of time and depiction of a variation of an environmental factor during the period of time.

13. The system of claim 12, wherein the wearable detector device includes the processing circuit and the user interface.

14. The system of claim 12, wherein the at least one biomarker comprises:
    at least one first biomarker associated with a T helper 1 (Th1) cell; and
    at least one second biomarker associated with a T helper 2 (Th2) cell.

15. The system of claim 14, wherein each of the at least one first biomarker and the at least one second biomarker comprises a cytokine, a chemokine, a metalloproteinase, a toxicity biomarker, or an antigen.

16. The system of claim 15, wherein the wellness data is associated with the relative amount of the T helper 1 (Th1) cell and the T helper 2 (Th2) cell in the biologic sample.

17. The system of claim 12, wherein the processing circuit is further configured to execute the program instructions to:
    generate a second data based upon either a personal factor or an environmental factor.

18. The system of claim 17, wherein the processing circuit is further configured to execute the program instructions to generate wellness data based upon one or more of the group consisting of:
    a sleep period of an individual;
    a medication taken by an individual; and
    a consumption of a substance by an individual.

19. The system of claim 17, wherein the processing circuit is further configured to execute the program instructions to generate the second data based upon one or more of the group consisting of:
    a location of an individual;
    an environmental condition around an individual; and
    an activity of an individual.

20. The system of claim 17, wherein the processing circuit is further configured to execute the program instructions to:

generate the second data based upon a personal factor and an environmental factor.

* * * * *